(12) United States Patent
Jun

(10) Patent No.: US 9,750,435 B2
(45) Date of Patent: Sep. 5, 2017

(54) SYSTEM, TERMINAL, AND METHOD FOR DIGITAL ELECTROCARDIOGRAM AUTHENTICATION

(71) Applicant: Moon-Seog Jun, Seoul (KR)

(72) Inventor: Moon-Seog Jun, Seoul (KR)

( * ) Notice: Subject to any disclaimer, the term of this patent is extended or adjusted under 35 U.S.C. 154(b) by 0 days.

(21) Appl. No.: 15/178,415

(22) Filed: Jun. 9, 2016

(65) Prior Publication Data
US 2016/0360998 A1    Dec. 15, 2016

(30) Foreign Application Priority Data

Jun. 11, 2015    (KR) .................. 10-2015-0082898

(51) Int. Cl.
| | | |
|---|---|---|
| *G05B 19/00* | (2006.01) | |
| *A61B 5/117* | (2016.01) | |
| *A61B 5/0408* | (2006.01) | |
| *A61B 5/04* | (2006.01) | |
| *A61B 5/0456* | (2006.01) | |
| *A61B 5/00* | (2006.01) | |

(52) U.S. Cl.
CPC .......... *A61B 5/117* (2013.01); *A61B 5/04012* (2013.01); *A61B 5/0456* (2013.01); *A61B 5/04085* (2013.01); *A61B 5/681* (2013.01)

(58) Field of Classification Search
None
See application file for complete search history.

(56) References Cited

U.S. PATENT DOCUMENTS

| | | | | | |
|---|---|---|---|---|---|
| 3,673,389 | A | * | 6/1972 | Kapsambelis ... | G06K 19/06009 194/212 |
| 3,874,370 | A | * | 4/1975 | Harris ................. | A61B 5/04365 600/515 |
| 4,829,296 | A | * | 5/1989 | Clark .................. | G07C 9/00309 232/7 |
| 5,680,134 | A | * | 10/1997 | Tsui .................... | G07C 9/00182 340/12.22 |
| 5,762,068 | A | * | 6/1998 | dePinto .................. | H03H 17/04 128/901 |
| 5,841,390 | A | * | 11/1998 | Tsui .................... | G07C 9/00182 340/12.5 |
| 6,005,508 | A | * | 12/1999 | Tsui .................... | G07C 9/00182 340/12.23 |
| 6,025,785 | A | * | 2/2000 | Farris ................. | G07C 9/00817 340/12.29 |
| 6,256,737 | B1 | * | 7/2001 | Bianco ............... | G07C 9/00158 713/186 |

(Continued)

FOREIGN PATENT DOCUMENTS

| | | |
|---|---|---|
| KR | 10-2013-0140439 A | 12/2013 |
| KR | 10-2014-0105903 A | 9/2014 |

(Continued)

*Primary Examiner* — Curtis King
(74) *Attorney, Agent, or Firm* — Novick, Kim & Lee, PLLC; Jae Youn Kim

(57) ABSTRACT

Provided is an electrocardiogram (ECG) biometric authentication system that performs biometric authentication using biometric information having unique values for each client includes one or more client terminals and a key distribution center (KDC) that uses ECG information of the one or more client terminals to issue a digital certificate. According to the configuration of the electrocardiogram biometric authentication system, security is enhanced.

2 Claims, 6 Drawing Sheets

(56) References Cited

U.S. PATENT DOCUMENTS

| | | | | |
|---|---|---|---|---|
| 6,310,966 B1* | 10/2001 | Dulude | G06Q 20/04 | 382/115 |
| 6,490,478 B1* | 12/2002 | Zhang | A61N 1/362 | 600/518 |
| 7,590,861 B2* | 9/2009 | Abdallah | H04L 9/3231 | 340/5.82 |
| 7,793,845 B2* | 9/2010 | Bonalle | G06Q 20/105 | 235/379 |
| 8,131,025 B2* | 3/2012 | Iseri | G06K 9/00006 | 340/5.53 |
| 8,234,128 B2* | 7/2012 | Martucci | A61B 5/0002 | 705/2 |
| 8,325,994 B2* | 12/2012 | Davida | G06F 21/32 | 340/5.53 |
| 8,775,196 B2* | 7/2014 | Simpson | G06F 19/3418 | 705/2 |
| 2003/0023881 A1* | 1/2003 | Fitzgibbon | G07C 9/00182 | 726/2 |
| 2004/0148508 A1* | 7/2004 | Alev | G06F 21/64 | 713/180 |
| 2004/0168069 A1* | 8/2004 | Knight | G07C 9/00158 | 713/186 |
| 2005/0027201 A1* | 2/2005 | Badilini | A61B 5/0402 | 600/509 |
| 2005/0071631 A1* | 3/2005 | Langer | H04L 9/0833 | 713/156 |
| 2005/0249239 A1* | 11/2005 | Pierce | G06F 19/3418 | 370/466 |
| 2005/0281439 A1* | 12/2005 | Lange | A61B 5/04525 | 382/115 |
| 2006/0136744 A1* | 6/2006 | Lange | G06K 9/00536 | 713/186 |
| 2006/0200670 A1* | 9/2006 | Kuffel | H04L 63/08 | 713/170 |
| 2007/0135866 A1* | 6/2007 | Baker | A61B 5/0002 | 607/60 |
| 2007/0225611 A1* | 9/2007 | Kumar | A61B 5/0006 | 600/523 |
| 2007/0236328 A1* | 10/2007 | Kraft | G07C 9/00182 | 340/5.26 |
| 2008/0162927 A1* | 7/2008 | Wang | H04L 9/0833 | 713/155 |
| 2008/0162943 A1* | 7/2008 | Ali | G07C 9/00158 | 713/185 |
| 2008/0183247 A1* | 7/2008 | Harding | A61N 1/0563 | 607/60 |
| 2009/0137916 A1* | 5/2009 | Maison-Blanche | A61B 5/046 | 600/516 |
| 2009/0303000 A1* | 12/2009 | Cowburn | G07D 7/2033 | 340/5.86 |
| 2010/0109835 A1* | 5/2010 | Alrabady | H04L 63/107 | 340/5.2 |
| 2010/0138668 A1* | 6/2010 | Tsuria | G06F 21/32 | 713/186 |
| 2010/0180111 A1* | 7/2010 | Hahn | H04W 12/06 | 713/150 |
| 2010/0228967 A1* | 9/2010 | Hahn | H04W 12/06 | 713/155 |
| 2010/0264752 A1* | 10/2010 | Wong | 307/116 | |
| 2010/0311482 A1* | 12/2010 | Lange | A61B 5/0404 | 463/1 |
| 2011/0254662 A1* | 10/2011 | Lindsay | G06F 19/322 | 340/5.82 |
| 2012/0002808 A1* | 1/2012 | Wang | B60R 25/04 | 380/44 |
| 2012/0068820 A1* | 3/2012 | Mollicone | G06F 21/00 | 340/5.82 |
| 2012/0075060 A1* | 3/2012 | Connor | G06F 19/327 | 340/5.54 |
| 2012/0124369 A1* | 5/2012 | Amenedo | H04L 63/0823 | 713/156 |
| 2012/0274444 A1* | 11/2012 | Micali | G07C 9/00031 | 340/5.65 |
| 2013/0172763 A1* | 7/2013 | Wheeler | A61B 5/0402 | 600/509 |
| 2013/0219387 A1* | 8/2013 | Moeller | G06F 9/4401 | 718/1 |
| 2013/0301830 A1* | 11/2013 | Bar-El | H04L 9/08 | 380/210 |
| 2014/0028438 A1* | 1/2014 | Kuenzi | G07C 9/00817 | 340/5.24 |
| 2014/0085050 A1* | 3/2014 | Luna | G07C 9/00087 | 340/5.82 |
| 2014/0163386 A1* | 6/2014 | He | A61B 5/7203 | 600/476 |
| 2014/0188770 A1* | 7/2014 | Agrafioti | A61B 5/117 | 706/13 |
| 2014/0225742 A1* | 8/2014 | Wenger | G01D 4/002 | 340/870.02 |
| 2014/0244998 A1* | 8/2014 | Amenedo | H04L 63/062 | 713/156 |
| 2014/0268964 A1* | 9/2014 | Xia | H02M 7/25 | 363/127 |
| 2015/0028996 A1* | 1/2015 | Agrafioti | G06F 21/40 | 340/5.82 |
| 2015/0278498 A1* | 10/2015 | Hong | G06F 21/32 | 340/5.82 |
| 2015/0326399 A1* | 11/2015 | Nigriny | H04L 9/3247 | 713/156 |
| 2016/0005026 A1* | 1/2016 | Bouffioux | G06F 21/32 | 705/44 |
| 2016/0048671 A1* | 2/2016 | Munafo | G06F 21/32 | 340/5.82 |
| 2016/0063231 A1* | 3/2016 | Bae | G06F 21/32 | 340/5.82 |
| 2016/0189451 A1* | 6/2016 | Yoo | A61B 5/117 | 340/5.82 |
| 2016/0342782 A1* | 11/2016 | Mullins | G02B 27/0176 | |
| 2017/0085380 A1* | 3/2017 | Pandrangi | H04L 9/321 | |

FOREIGN PATENT DOCUMENTS

| | | |
|---|---|---|
| KR | 10-2015-0029105 A | 3/2015 |
| WO | 99/34554 A2 | 7/1999 |

\* cited by examiner

SYSTEM, TERMINAL, AND METHOD FOR DIGITAL ELECTROCARDIOGRAM AUTHENTICATION

CROSS-REFERENCE TO RELATED APPLICATION

This application claims priority to and the benefit of Korean Patent Application No. 10-2015-0082898, filed on Jun. 11, 2015, the disclosure of which is incorporated herein by reference in its entirety.

BACKGROUND

1. Field of the Invention

The present invention relates to a terminal, system, and method for electrocardiogram (ECG) biometric authentication, and more particularly, to an ECG biometric authentication terminal, a biometric authentication system using the same, and a method thereof in which currents flowing in a body are generated when depolarization and repolarization occurs in an atrium/ventricle of the heart, and changes of the currents are measured and quantized to be converted into a digital binary code to facilitate determining similarities between the currents and improve reliability because similarities can only be determined through an image and a processing method is complex and unreliable when the measured changes of the currents are shown as waveforms on an analog graph such that the present invention provides a client terminal in the form of a smart watch used by coming into contact with a client's skin, changes QRS complex information unique to each individual into a digital code while extracting ECG information, and uses a Rivest-Shamir-Adleman (RSA)/Elliptic Curve Cryptosystem (ECC) algorithm to execute an authentication process by utilizing QRS complex digital ECG information as a private key of an asymmetric cryptographic system in which a public key and the private key form a pair.

2. Discussion of Related Art

Generally, a technology of utilizing various signals or data that can be extracted from a living body to use the signals or data in various types of systems is being advanced. For example, a biometric authentication technology which uses biometric signals or data to construct a security system has recently been coming into the spotlight.

A biometric authentication technology refers to a technology of authenticating a user by extracting signals or data related to a living body from the user, comparing the signals or data with pre-stored data, and confirming that the user is the user. Since the biometric authentication technology uses unique biometric signals or data of an individual unlike an identification (ID) card or a password, the biometric authentication technology is coming into the spotlight in the security field due to not having concerns of theft or loss and being difficult to forge or falsify.

In addition, the biometric authentication technology is also applicable in fields such as financial services, communication services, information security, the medical field, public safety management, and electronic commerce. In addition, although inputting a password or drawing a pattern exists as a method for authenticating a user in a portable terminal, a user authentication method using the biometric authentication technology is recently being developed to improve accuracy in authenticating a user.

Fingerprints, veins, irises, voices, faces, or lines on palms are commonly being utilized in the biometric authentication technology. Particularly, the most common method among biometric authentication methods being applied to security systems is a fingerprint recognition technology. Although fingerprints have been used for a long time as a biometric authentication method due to their characteristics of not changing for a lifetime, there is a problem in which accuracy is degraded when fingerprints are faded or dry or when fingers are stained with foreign substances.

In addition, a voice recognition technology using information on pitches of sounds according to intonations and speaking habits exist as a biometric authentication technology. Although the voice recognition technology has advantages of being able to authenticate a user even from a remote place and not requiring separate training related to a method of use, there is a disadvantage of having difficulty in authentication in a case of a hoarse throat due to cold and the like, and there is also a problem in which accuracy of authentication is degraded when others imitate a user's voice or background noise is high.

Consequently, a technology of recognizing a living body using electrocardiograms (ECGs) among biometric signals is recently being developed to solve the above problems of the biometric authentication technology.

In FIG. 1, ECG analog signals that represent normal heartbeats and electrical signals generated as a result of the heartbeats are displayed using P, QRS, T, and U waveforms.

An ECG refers to a record of electrical signals generated in the heart. A part referred to as "sinoauricular node" is present in the heart. The sinoauricular node is a particular part of the heart that controls heartbeats by cyclically generating electricity and inducing contraction of the heart.

Electrical signals generated from the sinoauricular node are transmitted throughout the heart along an electrical conduction system in the heart. Cells that form heart muscles contract due to the electrical signals transmitted to each part of the heart and cause the heart to beat. Here, a record of the electrical signals transmitted to the heart measured using electrodes attached to skin is referred to as the ECG. Electrodes are attached to various parts of the body, and an electrical phenomenon in each part of the heart can be understood well through the electrodes.

The biometric authentication technology using an ECG can be utilized in a security technology. That is, the biometric authentication technology using an ECG can be utilized as a technology for authenticating a user by extracting ECG signals from the user and comparing the extracted ECG signals with pre-stored ECG signals of a registered user. However, in this case, high accuracy of authentication is required to utilize ECG signals in user authentication and security technologies. A method of determining similarities between the extracted ECG signals of the user and the pre-stored ECG signals of the registered user is important for improving the accuracy of authentication. That is, accuracy of a method for determining similarities between the signals needs to be improved to use an ECG in a user authentication technology.

Conventionally, although image patterns have been extracted from analog ECG waveforms and the patterns have been compared to use an ECG in an authentication technology, this is unreliable since there are frequent errors in determining the similarities by comparing the image patterns.

Particularly, biometric authentication using image patterns is very insecure due to being replicable.

SUMMARY OF THE INVENTION

Consequently, the present invention has been devised to solve the above problems of the related art. A heart sends out a small amount of action currents every time it contracts, and an electrocardiogram (ECG) is a recording of electrical changes generated due to heartbeats on a body surface as waveform curves using an electrocardiograph as illustrated in FIG. 1. Since ECG measurement can be conveniently performed through the body surface, and the result provides a large amount of information on heart activity as well as being unique to each individual, it is an aspect of the present invention to provide an ECG biometric authentication terminal utilized in biometric authentication for confirming a client, a biometric authentication system using the same, and a method thereof.

It is another aspect of the present invention to provide an ECG biometric authentication terminal capable of confirming a client in real-time by grafting ECG measurement and processing technologies onto a smart device used by coming into contact with a client's body surface at all times or as needed, a biometric authentication system using the same, and a method thereof.

It is yet another aspect of the present invention to provide an ECG biometric authentication terminal that uses a Rivest-Shamir-Adleman (RSA)/Elliptic Curve Cryptosystem (ECC) algorithm to enhance security by utilizing a client's ECG information as a private key of an asymmetric cryptographic system in which a public key and the private key form a pair, a biometric authentication system using the same, and a method thereof.

To achieve objectives mentioned above, according to an aspect of the present invention, an ECG biometric authentication system of the present invention which is a biometric authentication system that performs biometric authentication using cyclical biometric voltage information having unique values for each client includes one or more client terminals and a key distribution center (KDC) that uses ECG information of the one or more client terminals to issue a digital certificate.

According to another aspect of the present invention, an ECG biometric authentication terminal of the present invention includes a smart band that surrounds a client's wrist, has one or more biometric electrodes coming into contact with skin of the wrist embedded therein, and detects analog ECG electrical signals through the one or more biometric electrodes, and a smart watch electrically connected to the one or more biometric electrodes to collect the analog ECG electrical signals and encode the analog ECG electrical signals into digital signals.

According to yet another aspect of the present invention, an ECG biometric authentication method of the present invention which is a method for a client terminal to be issued with a certificate from a KDC using an ECG includes collecting, by the client terminal, analog ECG waveform information in which upward pulses and downward pulses are displayed as a continuous curve, quantizing the analog ECG waveform information so that the analog ECG waveform information has discontinuous and unique ECG information values, and binarizing the ECG information values which has become unique by the quantization to generate a binary code.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
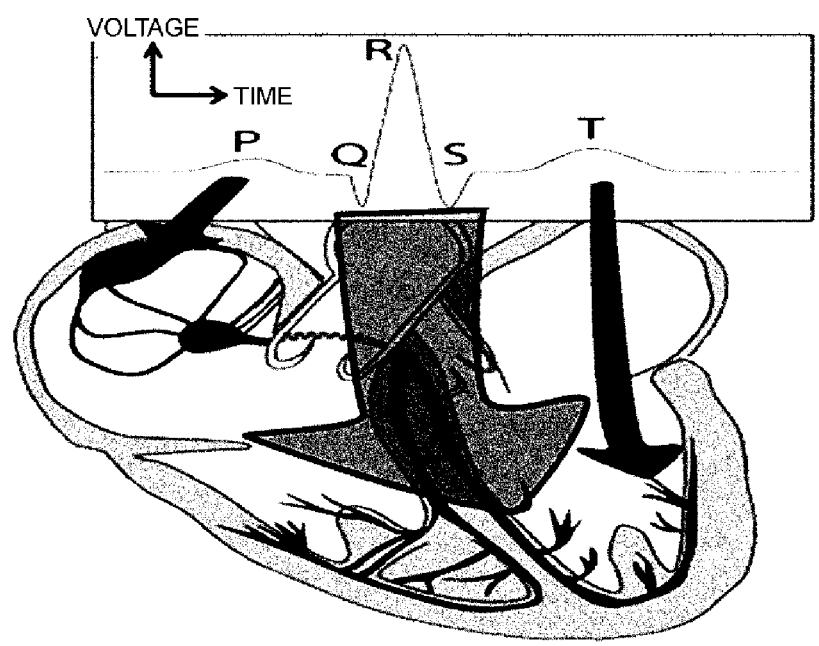
FIG. 1 is a view illustrating a graph showing P, QRS, T, and U waveforms that form electrocardiogram (ECG) analog signals and a heart which is the cause of the waveforms according to the related art.

Advantages and features of the present invention and a method for achieving the same will become apparent with reference to embodiments described in detail below and the accompanying drawings. However, the present invention is not limited to the embodiments disclosed hereinafter and may be implemented in various other forms. The embodiments are merely for completing the disclosure of the present invention, are provided to fully inform those of ordinary skill in the art to which the present invention pertains of the scope of the present invention, and are merely defined by the scope of the claims. Sizes and relative sizes of layers and regions in the drawings may be exaggerated for clarity of description. Like reference numerals refer to like elements throughout the specification.

Hereinafter, a preferred embodiment of an electrocardiogram (ECG) biometric authentication system according to the present invention having the configuration mentioned above will be described in detail with reference to the accompanying drawings.

Figure 2:
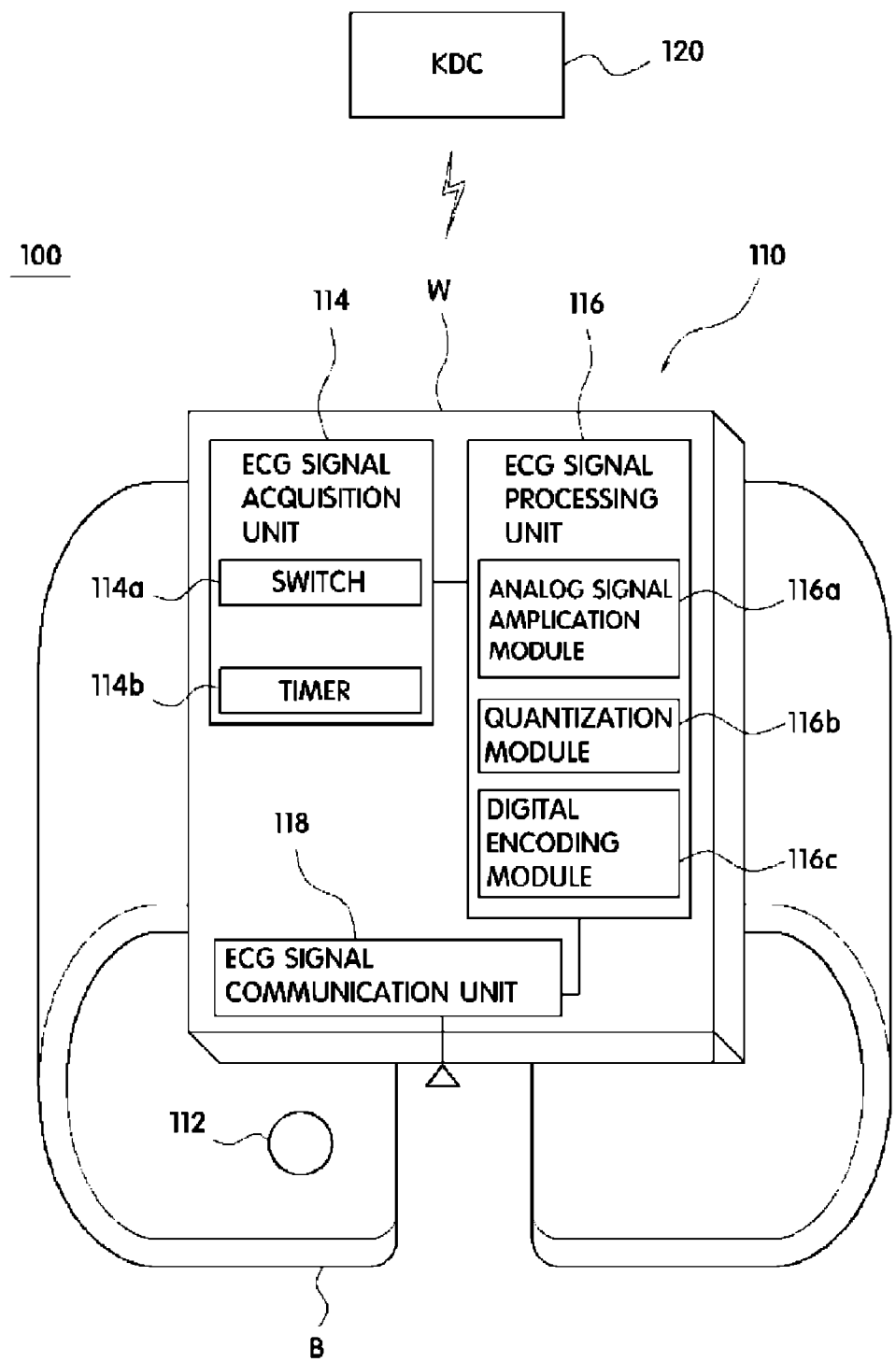
FIG. 2 is a block diagram illustrating a configuration of an ECG biometric authentication system according to the present invention.

In FIG. 2, a configuration of a system in which ECG biometric authentication is performed by an ECG biometric authentication terminal being connected over a network to a key distribution center (KDC) is illustrated in a block diagram.

Referring to FIG. 2, an ECG biometric authentication system 100 of the present invention includes one or more client terminals 110 and a KDC 120 that uses ECG biometric information to execute biometric authentication of a client. Although there are various types of biometric authentication (electroencephalogram, ECG, electromyogram, electrooculogram, etc.), the present invention uses ECG authentication among the above through which electrical changes according to a number of heartbeats are displayed and are easily acquirable in everyday lives and are particularly difficult to replicate.

The client terminal 110 includes an ECG measurement sensor 112, an ECG signal acquisition unit 114, an ECG signal processing unit 116, and an ECG signal communication unit 118.

The ECG measurement sensor 112 is formed of one or more biometric electrodes. The one or more biometric electrodes may be formed of snap electrodes that can be used for a long time without irritating a client's skin.

The ECG signal acquisition unit 114 is connected via a wire to the ECG measurement sensor 112 to collect and process ECG signals from the one or more biometric electrodes. The ECG signals collected by the ECG signal acquisition unit 114 are analog electrical signals. As illustrated in FIG. 2, analog electrical signals having particular voltage waveforms are provided from the one or more biometric electrodes.

The ECG signal acquisition unit 114 may include a switch 114a that determines a measurement time in real time when it is determined that measuring an ECG signal and converting the ECG signal to a digital code required for biometric authentication is needed. Alternatively, the ECG signal acquisition unit 114 may include a timer 114b capable of determining a measurement cycle when cyclical measurement is required.

For example, slight differences may be generated when ECG measurement is performed while resting and after exercising, while lying down and sitting down, or before eating or drinking and after eating or drinking. Thus, the switch 114a or the timer 114b may be used to select a proper measurement time, or an average value of information acquired through measurement for a predetermined amount of time or repeated measurement may be used when executing biometric authentication to prevent an authentication error.

The ECG signal processing unit 116 performs a function of converting analog electrical signals having continuously changing amplitudes (voltage levels) on a continuous time axis into discontinuous digital signals (codes) that change by integers in predetermined units.

Figure 4:
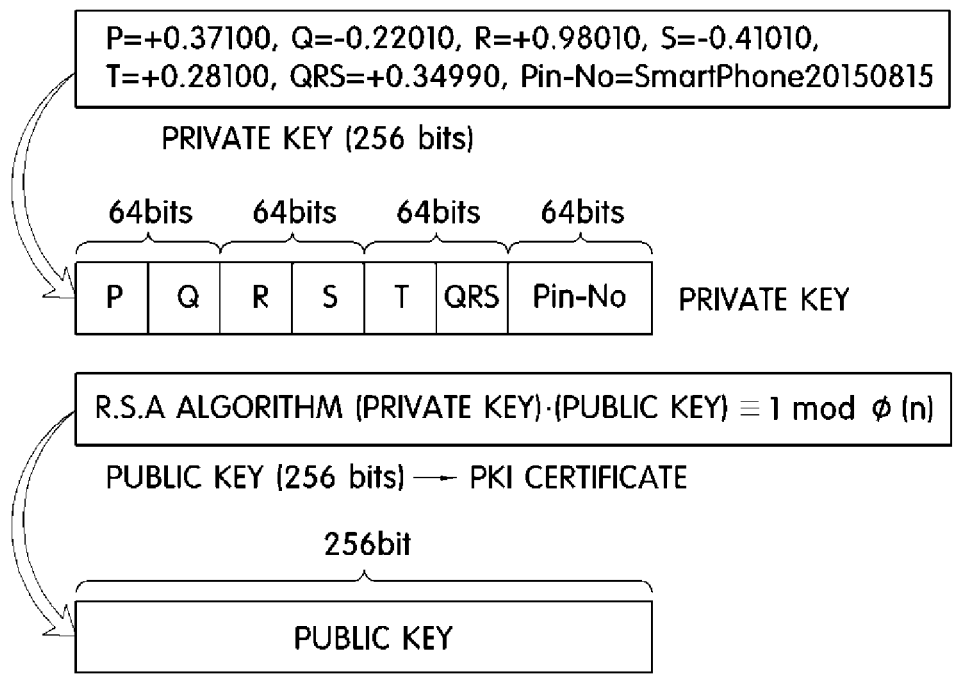
FIG. 4 is a conceptual view illustrating a digital code that quantizes the analog ECG electrical signals having particular voltage waveforms to generate a private key and a public key according to the present invention.

For this, the ECG signal processing unit 116 firstly amplifies sizes of the analog electrical signals through an analog signal amplification module 116a. The ECG signal processing unit 116 quantizes the analog electrical signals having particular waveforms through a quantization module 116b as illustrated in FIG. 4. In this way, the continuous analog electrical signals may be quantized based on a predetermined voltage level and be marked as P(+0.37100), Q(−0.22010), R(+0.98010), S(−0.41010), T(+0.28100), QRS(+0.34990), etc. Here, QRS is marked as (Q+R+S). The quantization result may be output as quantum codes which are decimals with five digits formed only of "1(or high),"0 (or middle)," and "−1(or low)" through a digital encoding module 116c.

The heart (refer to FIG. 1) is formed of two atriums and two ventricles. The heart generates micro-electricity every predetermined cycle by energy obtained from food and beats in the order of P, QRS, and T. In this way, the heart has a cardiac cycle from a predetermined heartbeat until a following heartbeat, and the cardiac cycle is divided into an atrial systolic period, a ventricular systolic period, and an atrial/ventricular diastolic period. A left atrium and a right atrium are contracted and a left ventricle and a right ventricle are relaxed in the atrial systolic period, the left atrium and the right atrium are relaxed and the left ventricle and the right ventricle are contracted in the ventricular systolic period, and the left and right atriums and the left and right ventricles are all relaxed in the atrial/ventricular diastolic period.

Referring again to FIG. 3, an ECG is represented as wave frequencies that have recorded action currents and action potential differences due to a contraction of the heart being recorded as a waveform curve. Upward pulses and downward pulses are alternatively repeated in the ECG waveform, and the pulses are referred to as a P-wave, a Q-wave, an R-wave, an S-wave, and a T-wave, in that order.

Figure 3:
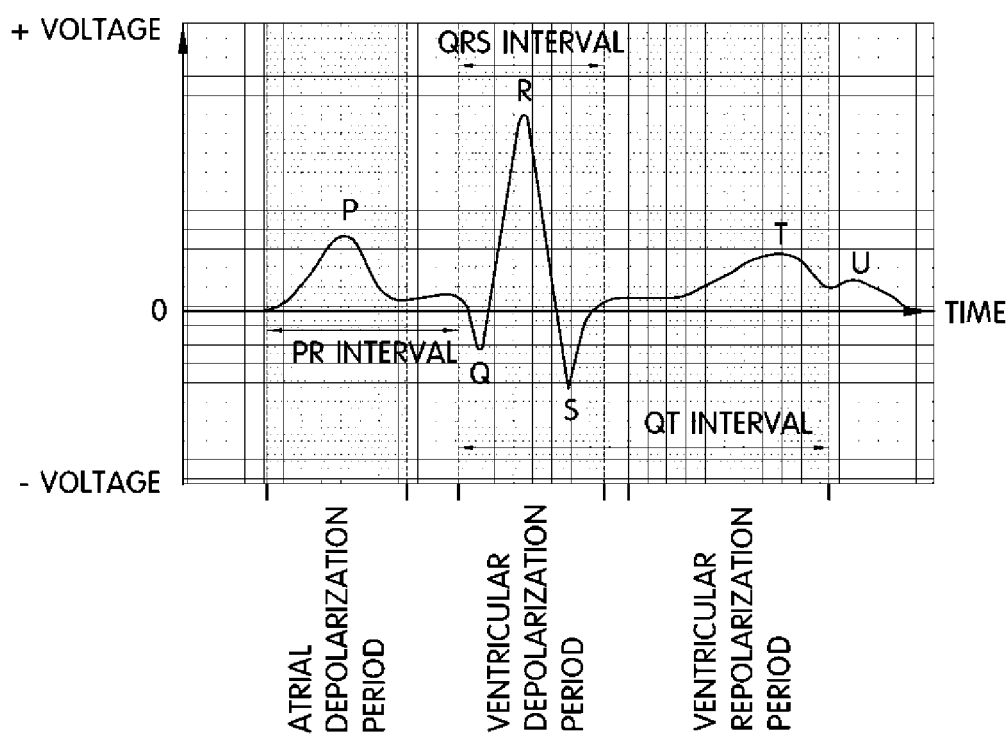
FIG. 3 is a graph illustrating analog ECG electrical signals having particular voltage waveforms obtained from biometric electrodes according to the present invention.

Here, the P-wave in FIG. 3 is a waveform that has recorded a systolic process of the left and right atriums, the QRS complex is a waveform that has recorded a systolic process of the left and right ventricles, and the T-wave is a waveform that has recorded a diastolic process of the left and right ventricles. The P-wave is generated in a depolarization period of the atriums, the QRS complex is generated in a depolarization period of the ventricles, and the T-wave is generated in a repolarization period of the ventricles.

The depolarization of the atriums and ventricles and repolarization of the ventricles of the heart may be measured on a surface of the client's skin. Consequently, the present invention aims to measure influences of the depolarization and repolarization using the client terminal 110 using the ECG measurement sensor 112.

Referring again to FIG. 4, the analog ECG waveforms are converted into binary digital codes through a quantization process. ECG digital information may represent 256-bit information by being formed of quantum codes of P-wave information (32-bit), Q-wave information (32-bit), R-wave information (32-bit), S-wave information (32-bit), T-wave information (32-bit), QRS complex information (32-bit), and PIN information (64-bit).

For example, as a result of detecting a P-wave, a Q-wave, an R-wave, an S-wave, a T-wave, and a QRS complex at an inflection point at which an upward pulse is changed to downward pulse (or a downward pulse is changed to an upward pulse) from an ECG waveform curve and extracting and quantizing the inflection point (a feature point), it can be seen that a P-wave information value, a Q-wave information value, an R-wave information value, an S-wave information value, a T-wave information value, and a QRS complex information value are displayed as "+0.37100," "−0.22010," "+0.98010," "−0.41010," "+0.28100," and "+0.34990," respectively. For example, as illustrated in FIG. 4, each pulse value may be quantized using a grid box.

Figure 5:
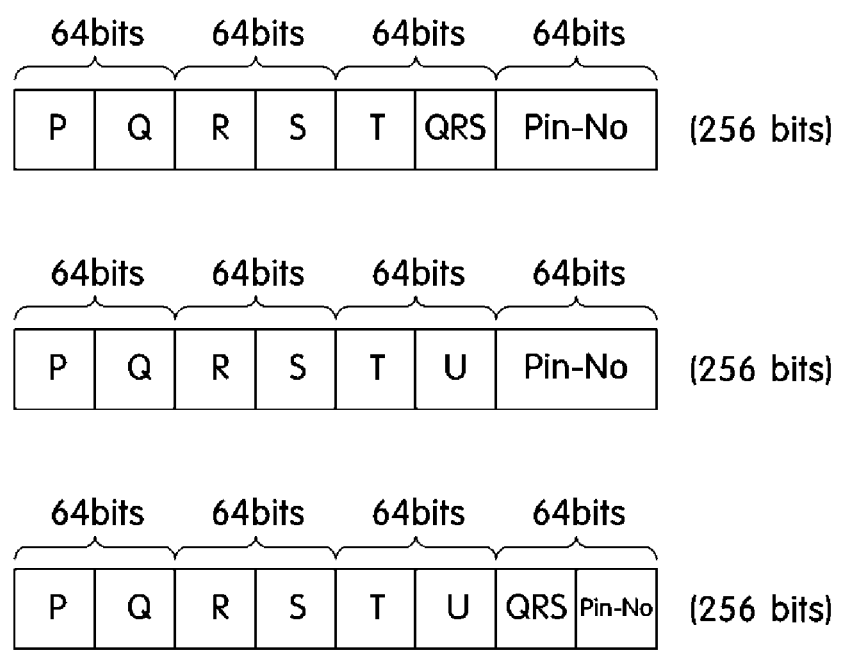
FIG. 5 is a conceptual view illustrating types of digital codes according to various embodiments of the present invention.

In yet another case, as illustrated in FIG. 5, a U-wave may be further included in addition to the P-wave, the Q-wave, the R-wave, the S-wave, the T-wave, and the QRS complex. However, the U-wave has a disadvantage compared to the QRS complex waveform in that upward pulses and downward pulses are clear and irregular. Consequently, still referring to FIG. 5, both of the U-wave and the QRS complex may be used.

Quantum code information values extracted from the ECG analog waveforms have values unique to each client, and the unique values may be used as information for biometric authentication of the present invention.

The ECG signal communication unit 118 has various communication functions such as communication via a mobile communications network, short-range wireless communication, etc. and may communicate in real-time with the KDC 120 that includes wireless communication modules such as a Bluetooth module capable of wireless data communication, an infrared communication module, a Zigbee module, etc.

Referring again to FIG. 2, a smart watch may be used as the client terminal 110 of the present invention. That is, the client terminal 110 includes a smart watch W and a smart band B that fixes the smart watch W to a wrist. The ECG measurement sensor 112, i.e., the biometric electrodes, may be installed in the smart band B that comes into contact with skin of the wrist. The smart band B may be a closed ring type that is flexible and contractible. Alternatively, the smart band B may be a fastening type that can be selectively opened or closed.

A smartphone, a personal digital assistant (PDA), a handheld personal computer (PC), a mobile phone, a home server PC, etc. may be used as the smart watch W.

The smart band B may be provided in the form of a patch to easily come into contact with skin to most effectively detect influences of depolarization and repolarization of the heart. The smart band B surrounds the client's wrist and allows the biometric electrodes to correspond to the skin of the wrist.

Consequently, among elements of the client terminal 110, the ECG measurement sensor 112 is embedded in the smart band B, the ECG signal acquisition unit 114, the ECG signal processing unit 116, and the ECG signal communication unit 118 that collect, process, and communicate ECG signals are embedded in the smart watch W, and the ECG measurement sensor 112 and the ECG signal acquisition unit 114 may perform wired or wireless communication with each other via the smart band B.

Next, referring to FIG. 4, the present invention may utilize the quantum codes determined by the method above to encrypt a private key.

The present invention uses a particular algorithm to encrypt data. Here, data encryption refers to a type of a lock in which data is transformed using a particular algorithm to prevent an unauthorized person from accessing the data. In this case, the particular algorithm being used serves as a key for locking the lock.

Conversely, to reproduce the encrypted data mentioned above, a means capable of decrypting the particular algorithm used in the encryption should be provided. The means for decrypting the particular algorithm serves as a key for unlocking the lock. That is, when the key is provided, the key may be used to decrypt the algorithm used in encrypting the data, and the data may be decrypted into an original form. Consequently, the algorithms used in encryption and decryption of the data are referred to as keys.

The present invention uses an asymmetric cryptographic system in which a key used for encryption and a key used for decryption are different. The asymmetric cryptographic system is an encryption technique in which a key used for encryption and a key used for decryption are different and is also referred to as a cryptosystem.

For example, the asymmetric cryptographic system is generally characterized as a public key infrastructure (PKI). A public key and a private key are configured by a product of two large decimals (normally a number with 140 digits or more) and additional computations, and a user is authenticated through a digital certificate.

Hereinafter, a process of issuing a client terminal with a certificate from the KDC using an ECG will be described with reference to the drawings.

Figure 6:
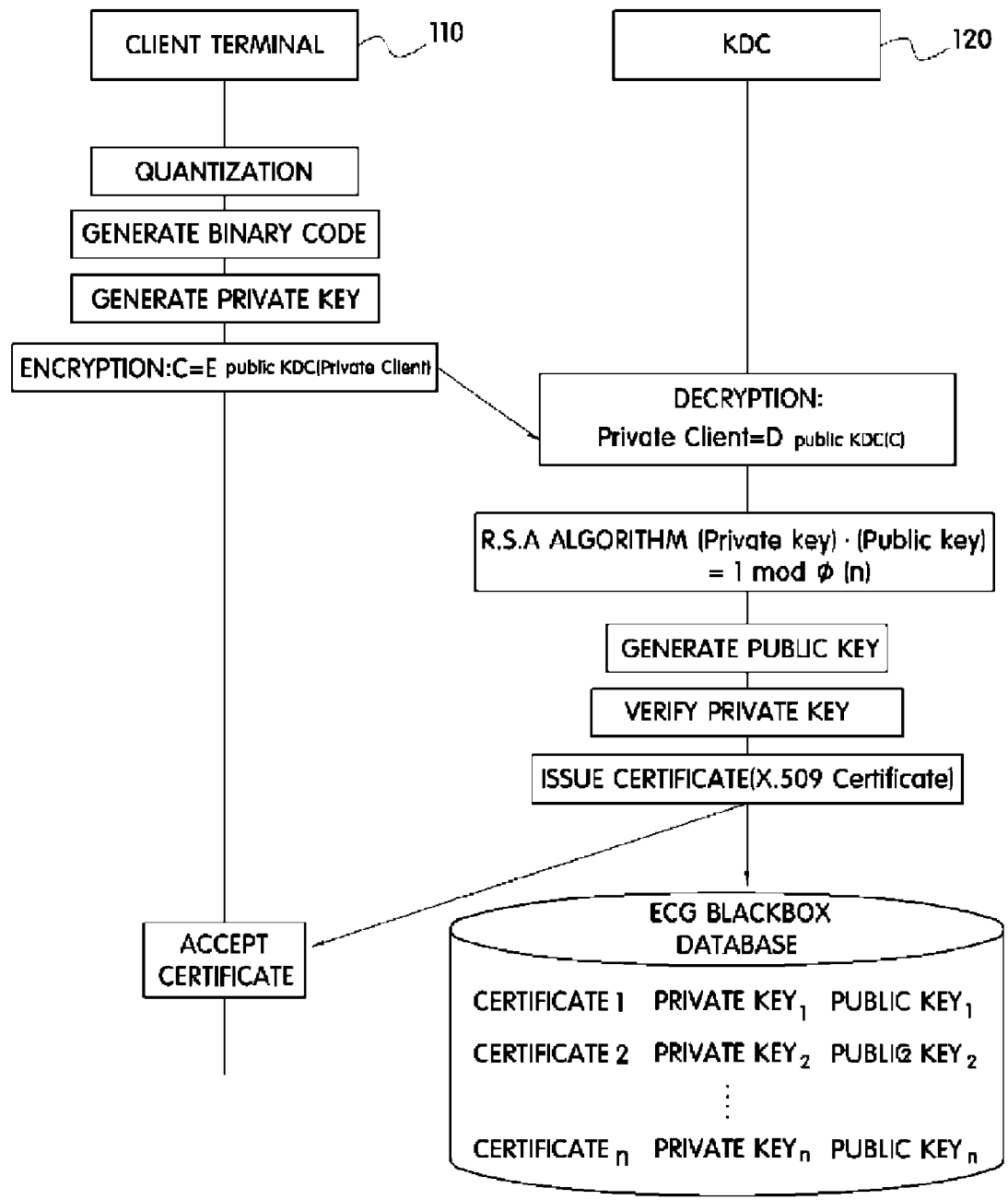
FIG. 6 is a flowchart illustrating a process of ECG biometric authentication according to the present invention.

Referring to FIG. 6, analog ECG waveform information in which upward/downward pulses are displayed as a continuous curve is quantized. The quantized discontinuous ECG information values have unique values.

A 256-bit private key is generated using each ECG waveform information value that has become unique by quantization. The private key of this degree is a sufficient number that enables all animals to be used as unique keys.

Encryption is performed by generating a pair of keys formed of the private key and a public key. The encryption result is transmitted to the KDC 120.

The KDC 120 decrypts the encryption result to generate the public key. Here, the KDC 120 issues a certificate using the RSA/ECC algorithm. In this case, PKI authentication is executed by providing the public key using the RSA/ECC algorithm.

The client terminal 110 receives the certificate and uses the certificate in the authentication process. The certificate is a digital document that proves that the particular client terminal 110 owns the corresponding public key.

Meanwhile, after the client terminal 110 has finished the authentication through the above-mentioned process of being issued with the digital certificate from the KDC 120, the client terminal 110 may restart the authentication process when the digital certificate needs to be renewed. Here, one hour may be set by the timer 114b, and when a private key is not received by the KDC 120 based on ECG information from the client terminal 110 during the set amount of time, the authentication process may be completely cancelled and be newly executed from a starting point to further enhance security.

The ECG biometric authentication terminal of the present invention is provided in the form of a smart watch and may be applied to an electronic bracelet that is worn by a particular criminal for surveillance of the criminal. A state in which the electronic bracelet is worn can be checked from a remote place by ECG information of the individual criminal being sent to the KDC in real-time or periodically.

As described above, the following effects can be expected by the configuration of the present invention.

First, an ECG biometric authentication terminal is in contact with a client's skin all the time such that it is convenient to perform real-time authentication and security is considerably enhanced due to authentication being completely impossible when the ECG biometric authentication terminal is detached from the client.

Second, a private key generated by processing QRS complex information unique to each individual to be quantized into digital codes through a quantization process is applied to a public key algorithm that uses a public key-private key combination such that security is further enhanced.

As described above, it can be recognized that the technical spirit of the present invention is a configuration in which an ECG biometric authentication terminal is provided in the form of a smart watch such that biometric electrodes that measure heartbeats can be installed in a band that is in contact with a client's wrist all the time, a function of quantizing analog ECG waveforms to process the analog ECG waveforms to be converted into digital codes is embedded in a main body of a smart device such that the smart device may be used for its original function as well as for authentication during mobile banking and other payments processed using the smart device, and the digital codes acquired by processing the ECG waveforms are utilized in an RSA/ECC algorithm to enhance security. Those of ordinary skill in the art will be able to modify the present invention in various other ways within the scope of the basic technical spirit of the present invention.

What is claimed is:

1. A method for a client terminal to be issued with a certificate from a key distribution center (KDC) using an electrocardiogram (ECG), the method comprising:

collecting, by the client terminal, analog ECG waveform information in which upward pulses and downward pulses are displayed as a continuous curve;

quantizing the analog ECG waveform information so that the analog ECG waveform information has discontinuous and unique ECG information values;

binarizing the ECG information values which has become unique by the quantization to generate a binary code;

changing the binary code into a private key and encrypting the private key and a public key;

transmitting, by the client terminal, the encrypted private and public keys to a key distribution center (KDC);

decrypting the encrypted public key, in the KDC, to generate the public key by using a Rivest-Shamir-Adleman (RSA)/Elliptic Curve Cryptosystem (ECC) algorithm;

transmitting the public key to the client terminal from the KDC; and executing authentication, by the client terminal, using the public key.

2. The method of claim 1, wherein, in decrypting the encrypted public key to generate the public key, the KDC uses the RSA/ECC algorithm to issue an ECG biometric private key verification and the certificate.

* * * * *